(12) United States Patent
Ben-Tsur

(10) Patent No.: US 10,537,720 B2
(45) Date of Patent: Jan. 21, 2020

(54) METHOD OF ENHANCING ABSORPTION OF INGESTED MEDICAMENTS FOR TREATMENT OF PARKINSONISM

(71) Applicant: VIBRANT LTD., Yokneam (IL)

(72) Inventor: Lior Ben-Tsur, Netanya (IL)

(73) Assignee: Vibrant Ltd., Yokneam (IL)

( * ) Notice: Subject to any disclaimer, the term of this patent is extended or adjusted under 35 U.S.C. 154(b) by 0 days.

(21) Appl. No.: 16/178,425

(22) Filed: Nov. 1, 2018

(65) Prior Publication Data

US 2019/0307999 A1 Oct. 10, 2019

Related U.S. Application Data

(60) Provisional application No. 62/655,031, filed on Apr. 9, 2018.

(51) Int. Cl.
*A61M 31/00* (2006.01)
*A61K 9/00* (2006.01)
*A61K 41/00* (2006.01)

(52) U.S. Cl.
CPC .......... *A61M 31/00* (2013.01); *A61K 9/0053* (2013.01); *A61K 41/0023* (2013.01);
(Continued)

(58) Field of Classification Search
CPC . A61K 41/0023; A61K 9/0053; A61M 31/00; A61M 37/00
See application file for complete search history.

(56) References Cited

U.S. PATENT DOCUMENTS 3,485,235 A 12/1969 Felson
4,507,115 A 3/1985 Kambara et al.
(Continued)

FOREIGN PATENT DOCUMENTS

CN 1829466 A 9/2006
CN 102743174 A 10/2012
(Continued)

OTHER PUBLICATIONS

'Smart capsule to target colon diseases', Ben Gruber, Sep. 30, 2015 https://www.reuters.com/article/us-smart-capsule-colon-idUSKCN0RU1ZE20150930.
(Continued)

*Primary Examiner* — William R Carpenter
(74) *Attorney, Agent, or Firm* — Marc Van Dyke; Momentum IP Group

(57) ABSTRACT

A method of using a vibrating gastrointestinal capsule in coordination with an ingestible medicament for treatment of Parkinsonism. The vibrating gastrointestinal capsule, is provided to the subject, and includes: a housing; a vibrating agitation mechanism causing said housing to exert vibrations on an environment surrounding the vibrating gastrointestinal capsule; a power supply for powering said vibrating agitation mechanism; and a control mechanism for activating said vibrating agitation mechanism to operate in said vibration mode of operation. The subject ingests the ingestible medicament and the vibrating gastrointestinal capsule. At least one of a time of ingesting of the vibrating gastrointestinal capsule and a timing or activation delay of the vibration mode of operation is controlled, such that the vibration mode of operation at least partially transpires or completely transpires within an actual or estimated absorption time period of the ingestible medicament within the gastrointestinal tract of the subject.

17 Claims, 2 Drawing Sheets

(52) U.S. Cl.
CPC ............... *A61M 2205/3306* (2013.01); *A61M 2205/3327* (2013.01); *A61M 2205/3341* (2013.01); *A61M 2205/3368* (2013.01)

(56) References Cited

U.S. PATENT DOCUMENTS

| | | | |
|---|---|---|---|
| 5,170,801 | A | 12/1992 | Casper et al. |
| 6,632,216 | B2 | 10/2003 | Houzego et al. |
| 6,776,165 | B2 | 8/2004 | Jin |
| 6,929,363 | B2 | 8/2005 | Sakai et al. |
| 6,984,205 | B2 | 1/2006 | Gazdzinski |
| 8,202,697 | B2 | 6/2012 | Holmes |
| 8,518,022 | B2 | 8/2013 | Trovato et al. |
| 8,597,278 | B2 | 12/2013 | Trovato et al. |
| 8,701,677 | B2 | 4/2014 | Duan et al. |
| 9,078,799 | B2 | 7/2015 | Shohat et al. |
| 9,156,169 | B2 | 10/2015 | Duan et al. |
| 9,232,909 | B2 | 1/2016 | Duan et al. |
| 9,532,923 | B2 | 1/2017 | Shohat et al. |
| 9,707,150 | B2 | 7/2017 | Shabbat |
| 2002/0132226 | A1 | 9/2002 | Nair et al. |
| 2003/0020810 | A1 | 1/2003 | Takizawa et al. |
| 2004/0030454 | A1 | 2/2004 | Kim et al. |
| 2004/0253304 | A1 | 12/2004 | Gross et al. |
| 2004/0267240 | A1 | 12/2004 | Gross et al. |
| 2005/0058701 | A1 | 3/2005 | Gross et al. |
| 2005/0085696 | A1 | 4/2005 | Uchiyama et al. |
| 2005/0148847 | A1 | 7/2005 | Uchiyama et al. |
| 2005/0177069 | A1 | 8/2005 | Takizawa et al. |
| 2006/0169293 | A1 | 8/2006 | Yokoi et al. |
| 2006/0276729 | A1 | 12/2006 | Reed et al. |
| 2007/0015952 | A1 | 1/2007 | Chang et al. |
| 2007/0238940 | A1 | 10/2007 | Amirana |
| 2008/0188837 | A1 | 8/2008 | Belsky et al. |
| 2008/0275430 | A1 | 11/2008 | Belsky et al. |
| 2009/0281380 | A1 | 11/2009 | Miller et al. |
| 2009/0306633 | A1 | 12/2009 | Trovato et al. |
| 2009/0318841 | A1 | 12/2009 | Shohat et al. |
| 2010/0049012 | A1 | 2/2010 | Dijksman et al. |
| 2010/0217079 | A1 | 8/2010 | Tichy |
| 2013/0267788 | A1 | 10/2013 | Duan et al. |
| 2015/0011829 | A1 | 1/2015 | Wang et al. |
| 2015/0018614 | A1 | 1/2015 | Duan et al. |
| 2015/0018615 | A1 | 1/2015 | Duan et al. |
| 2015/0073315 | A1 | 3/2015 | Shabbat |
| 2015/0380140 | A1 | 12/2015 | Duan et al. |
| 2016/0136104 | A1* | 5/2016 | Niichel ............... A61B 5/0002 604/131 |
| 2016/0287058 | A1 | 10/2016 | Ye et al. |
| 2016/0303133 | A1* | 10/2016 | Dudley ............... A61K 31/165 |
| 2016/0310357 | A1 | 10/2016 | Duan et al. |
| 2017/0020374 | A1 | 1/2017 | Duan et al. |
| 2017/0035407 | A1 | 2/2017 | Duan et al. |
| 2017/0035520 | A1 | 2/2017 | Duan et al. |
| 2017/0135897 | A1 | 5/2017 | Shohat et al. |
| 2017/0273863 | A1 | 9/2017 | Shabbat |
| 2017/0296425 | A1 | 10/2017 | Duan et al. |
| 2017/0296428 | A1 | 10/2017 | Duan et al. |
| 2017/0340242 | A1 | 11/2017 | Duan |
| 2018/0055597 | A1 | 3/2018 | Duan et al. |
| 2018/0084975 | A1 | 3/2018 | Duan et al. |

FOREIGN PATENT DOCUMENTS

| | | |
|---|---|---|
| CN | 102743175 A | 10/2012 |
| CN | 102743176 A | 10/2012 |
| CN | 202483565 U | 10/2012 |
| CN | 102813515 A | 12/2012 |
| CN | 102860810 A | 1/2013 |
| CN | 202699138 U | 1/2013 |
| CN | 202821355 U | 3/2013 |
| CN | 202843564 U | 4/2013 |
| CN | 202843608 U | 4/2013 |
| CN | 202875332 U | 4/2013 |
| CN | 103222842 A | 7/2013 |
| CN | 203634116 U | 6/2014 |
| CN | 104898850 A | 9/2015 |
| CN | 105025245 A | 11/2015 |
| CN | 105079970 A | 11/2015 |
| CN | 105411505 A | 3/2016 |
| CN | 205108749 U | 3/2016 |
| CN | 105939451 A | 9/2016 |
| CN | 105942959 A | 9/2016 |
| CN | 105996961 A | 10/2016 |
| CN | 106056588 A | 10/2016 |
| CN | 106097335 A | 11/2016 |
| CN | 106137760 A | 11/2016 |
| CN | 106204599 A | 12/2016 |
| CN | 205758500 U | 12/2016 |
| CN | 106373137 A | 2/2017 |
| CN | 205913317 U | 2/2017 |
| CN | 205928774 U | 2/2017 |
| CN | 106923787 A | 7/2017 |
| CN | 106934799 A | 7/2017 |
| CN | 107174188 A | 9/2017 |
| CN | 107233580 A | 10/2017 |
| CN | 107240091 A | 10/2017 |
| CN | 107375951 A | 11/2017 |
| EP | 2987447 A1 | 2/2016 |
| EP | 2995240 A1 | 3/2016 |
| JP | 2001062397 A | 3/2001 |
| JP | 2010503451 A | 2/2010 |
| WO | 2006025013 A1 | 3/2006 |
| WO | 2007013059 A2 | 2/2007 |
| WO | 2008012700 A1 | 1/2008 |
| WO | 2008035329 A2 | 3/2008 |
| WO | 2009063375 A1 | 5/2009 |
| WO | 2013121276 A1 | 8/2013 |
| WO | 2018055487 A1 | 3/2018 |

OTHER PUBLICATIONS

'Advanced Delivery Devices—IntelliCap: An Intelligent, Electronic Capsule for Oral Drug Delivery & Development', Drug Development & Delivery, Apr. 2013 http://drug-dev.com/advanced-delivery-devices-intellicap-an-intelligent-electronic-capsule-for-oral-drug-delivery-development/.
Machine Translation (by Google Patents) for CN 102743174 published on Oct. 24, 2012.
Machine Translation (by Google Patents) for CN 102743175 published on Oct. 24, 2012.
Machine Translation (by Google Patents) for CN 102743176 published on Oct. 24, 2012.
Machine Translation (by Google Patents) for CN 102813515 published on Dec. 12, 2012.
Machine Translation (by Google Patents) for CN 102860810 published on Jan. 9, 2013.
Machine Translation (by Google Patents) for CN 03222842 published on Jul. 31, 2013.
Machine Translation (by Google Patents) for CN 104898850 published on Sep. 9, 2015.
Machine Translation (by Google Patents) for CN 105025245 published on Nov. 4, 2015.
Machine Translation (by Google Patents) for CN 105079970 published on Nov. 25, 2015.
Machine Translation (by Google Patents) for CN 105411505 published on Mar. 23, 2016.
Machine Translation (by Google Patents) for CN 105939451 published on Sep. 14, 2016.
Machine Translation (by Google Patents) for CN 105942959 published on Sep. 21, 2016.
Machine Translation (by Google Patents) for CN 105996961 published on Oct. 12, 2016.
Machine Translation (by Google Patents) for CN 106056588 published on Oct. 26, 2016.
Machine Translation (by Google Patents) for CN 106097335 published on Nov. 9, 2016.
Machine Translation (by Google Patents) for CN 106137760 published on Nov. 13, 2016.

(56) References Cited

OTHER PUBLICATIONS

Machine Translation (by Google Patents) for CN 106204599 published on Dec. 7, 2016.
Machine Translation (by Google Patents) for CN 106373137 published on Feb. 1, 2017.
Machine Translation (by Google Patents) for CN 106923787 published on Jul. 7, 2017.
Machine Translation (by Google Patents) for CN 106934799 published on Jul. 7, 2017.
Machine Translation (by Google Patents) for CN 107174188 published on Sep. 19, 2017.
Machine Translation (by Google Patents) for CN 107233580 published on Oct. 10, 2017.
Machine Translation (by Google Patents) for CN 107240091 published on Oct. 10, 2017.
Machine Translation (by Google Patents) for CN 107375951 published on Nov. 24, 2017.
Machine Translation (by Google Patents) for CN 1829466 published on Sep. 6 2006.
Machine Translation (by Google Patents) for CN 202483565 published on Oct. 10, 2012.
Machine Translation (by Google Patents) for CN 202699138 published on Jan. 30, 2013.
Machine Translation (by Google Patents) for CN 202821355 published on Mar. 27, 2013.
Machine Translation (by Google Patents) for CN 202843564 published on Apr. 3, 2013.
Machine Translation (by Google Patents) for CN 202843608 published on Apr. 3, 2013.
Machine Translation (by Google Patents) for CN 202875332 published on Apr. 17, 2013.
Machine Translation (by Google Patents) for CN 203634116 published on Jun. 11, 2014.
Machine Translation (by Google Patents) for CN 205108749 published on Mar. 30, 2016.
Machine Translation (by Google Patents) for CN 205758500 published on Dec. 7, 2016.
Machine Translation (by Google Patents) for CN 205913317 published on Feb. 1, 2017.
Machine Translation (by Google Patents) for CN 205928774 published on Feb. 8, 2017.
Machine Translation (by Google Patents) for JP 2001062397 published on Mar. 13, 2001.
Machine Translation (by Google Patents) for JP 2010503451 published on Feb. 4, 2010.

* cited by examiner

METHOD OF ENHANCING ABSORPTION OF INGESTED MEDICAMENTS FOR TREATMENT OF PARKINSONISM

FIELD OF THE INVENTION

The present invention relates in general to vibrating capsule systems including one or more vibrating capsules, and to treatment methods using such systems and capsules, and more particularly, to vibrating capsule systems and methods for enhancing the absorption to the blood stream of an ingested medicament for treatment of Parkinsonism.

SUMMARY OF THE INVENTION

In accordance with an embodiment of the present invention, there is provided a vibrating ingestible capsule for promoting absorption of an ingested medicament into the blood stream, the vibrating ingestible capsule including:

a housing;

a vibrating agitation mechanism adapted such that, in a vibration mode of operation, the housing exerts vibrations on an environment surrounding the vibrating gastrointestinal capsule;

a power supply disposed within the housing and adapted to power the vibrating agitation mechanism; and a control mechanism adapted to activate the vibrating agitation mechanism to be operative in the vibration mode of operation, the control mechanism adapted to control a timing or activation delay of the vibration mode of operation such that the vibration mode of operation at least partially transpires within at least one of an estimated absorption time period and an actual absorption time period of the ingested medicament within the gastrointestinal tract of the subject.

In some embodiments, the control mechanism is adapted to activate the vibration agitation mechanism to be operative in the vibration mode of operation in response to receipt of an activation input.

In some embodiments, the vibrating ingestible capsule further includes at least one sensor adapted to provide the activation input.

In some embodiments, the at least one sensor includes an illumination sensor, and the receiving the at least one activation input includes receiving input indicating transition of the capsule from an illuminated environment to a dark environment.

In some embodiments, the at least one sensor includes a pressure sensor and the receiving the at least one activation input includes receiving input indicting pressure applied to the capsule, which pressure is indicative of the capsule moving through a pharynx of the subject.

In some embodiments, the at least one sensor includes a temperature sensor, and the receiving the at least one activation input includes receiving input indicating transition of the capsule from an area with ambient temperature to an area with a human body temperature.

In some embodiments, the at least one sensor includes an accelerometer, and the receiving the at least one activation input includes receiving the activation input in response to a detected activation motion carried out with the gastrointestinal capsule.

In some embodiments, the at least one sensor includes a moisture sensor, and the receiving the at least one activation input includes receiving input indicating transition of the capsule from a dry environment to a humid environment.

In some embodiments, the vibrating ingestible capsule is functionally associated with a control unit remote from the vibrating ingestible capsule, and the control mechanism is adapted to receive the activation input from the control unit remote.

In some embodiments, the control mechanism is adapted to receive the activation input following ingesting of the vibrating capsule.

In some embodiments, the control mechanism is adapted to receive the activation input prior to ingesting of the vibrating capsule.

In some embodiments, the control mechanism is adapted to receive the activation input by receiving a vibration protocol to be used by the control mechanism to control operation of the vibrating agitation mechanism.

In some embodiments, the vibrating agitation mechanism includes at least a radial agitation mechanism adapted, in the vibration mode of operation, to exert radial forces on the housing, in a radial direction with respect to a or the longitudinal axis of the housing, thereby to cause the vibrations exerted by the housing.

In some embodiments, the vibrating agitation mechanism includes at least an axial agitation mechanism adapted, in the vibration mode of operation, to exert axial forces on the housing, in an axial direction with respect to a or the longitudinal axis of the housing, thereby to cause the vibrations exerted by the housing.

In some embodiments, the vibrating agitation mechanism includes a radial agitation mechanism adapted to exert the radial forces and a separate axial agitation mechanism adapted to exert the axial forces.

In some embodiments, the vibrating agitation mechanism includes a single agitation mechanism adapted to exert the radial forces and the axial forces.

In some embodiments, the control mechanism is adapted to control the vibrating agitation mechanism such that the vibrating mode of operation includes a plurality of cycles, each of the cycles including a vibration duration followed by a repose duration, wherein the housing exerts the vibrations during the vibration duration.

In some embodiments, the repose duration is greater than the vibration duration.

In some embodiments, the vibration duration is in the range of 0.1 second to 10 seconds, 1 second to 10 seconds, 1 second to 9 seconds, 2 seconds to 9 seconds, 3 seconds to 9 seconds, 3 seconds to 8 seconds, 3 seconds to 7 seconds, 3 seconds to 6 seconds, 4 seconds to 6 seconds, or 5 seconds to 6 seconds.

In some embodiments, the repose duration is in the range of 1 second to 180 seconds, 3 seconds to 180 seconds, 5 seconds to 180 seconds, 5 seconds to 150 seconds, 5 seconds to 120 seconds, 8 seconds to 100 seconds, 8 seconds to 30 seconds, 10 seconds to 80 seconds, 10 seconds to 70 seconds, 10 seconds to 60 seconds, 10 seconds to 50 seconds, 10 seconds to 40 seconds, 10 seconds to 30 seconds, 10 seconds to 20 seconds, or 15 seconds to 20 seconds.

In some embodiments, a duration of each of the plurality of cycles is in the range of 1.1 seconds to 200 seconds, 5 seconds to 200 seconds, 10 seconds to 200 seconds, 10 seconds to 150 seconds, 10 seconds to 100 seconds, 10 seconds to 80 seconds, 10 seconds to 50 seconds, 10 seconds to 40 seconds, 10 seconds to 30 seconds, 15 seconds to 50 seconds, 15 seconds to 40 seconds, 15 seconds to 30 seconds, or 15 seconds to 25 seconds.

In some embodiments, the control mechanism is adapted to control the vibrating agitation mechanism such that a cumulative duration of the vibrating mode of operation is in the range of 1 hour to 12 hours, 2 hours to 10 hours, 2 hours to 8 hours, 2 hours to 6 hours, 2 hours to 4 hours, or 2 hours to 3 hours.

In some embodiments, in the first vibration mode of operation, the vibrating agitation mechanism is configured such that a net force exerted by the housing on the environment is in the range of 50 grams-force to 600 grams-force.

In some embodiments, in the first vibration mode of operation the vibrating agitation mechanism is configured to exert the forces on the housing to attain a vibrational frequency within a range of 10 Hz to 650 Hz, 15 Hz to 600 Hz, 20 Hz to 550 Hz, 30 Hz to 550 Hz, 50 Hz to 500 Hz, 70 Hz to 500 Hz, 100 Hz to 500 Hz, 130 Hz to 500 Hz, or 150 Hz to 500 Hz.

In accordance with another embodiment of the present invention, there is provided a method of using a vibrating gastrointestinal capsule in coordination with an ingestible medicament for treatment of Parkinsonism, the method including:

(a) providing the vibrating gastrointestinal capsule, the capsule including:
  a housing;
  a vibrating agitation mechanism adapted such that, in a vibration mode of operation, the housing exerts vibrations on an environment surrounding the vibrating gastrointestinal capsule;
  a power supply disposed within the housing and adapted to power the vibrating agitation mechanism; and
  a control mechanism adapted to activate the vibrating agitation mechanism to operate in the vibration mode of operation;
(b) ingesting the ingestible medicament;
(c) ingesting the vibrating gastrointestinal capsule; and
(d) controlling at least one of a time of the ingesting of the vibrating gastrointestinal capsule and a timing or activation delay of the vibration mode of operation, such that the vibration mode of operation at least partially transpires within at least one of an estimated absorption time period and an actual absorption time period of the ingestible medicament within the gastrointestinal tract of the subject.

In some embodiments, the controlling is effected such that the vibration mode of operation at least partially transpires during the actual absorption time.

In some embodiments, the actual absorption time period occurs when the ingestible medicament is disposed in a stomach of the subject. In some embodiments, the actual absorption time period occurs when the ingestible medicament is disposed in a small intestine of the subject. In some embodiments, the actual absorption time period occurs when the ingestible medicament is disposed in a large intestine of the subject.

In some embodiments, the controlling of is effected such that the vibration mode of operation at least partially transpires during the estimated absorption time. In some embodiments, the estimated absorption time is within a range of 0.5 to 1.5 hours. In some embodiments, the estimated absorption time is within a range of 1.0 to 5 hours. In some embodiments, the estimated absorption time is within a range of 0.5 to 5 hours. In some embodiments, the estimated absorption time is within a range of 4 to 30 hours.

In some embodiments, the ingesting of the vibrating gastrointestinal capsule transpires within 4 hours, within 3.5 hours, within 3 hours, within 2.5 hours, within 2 hours, within 1.5 hours, within 1 hour, or within 0.5 hours of, or after, the ingesting of the ingestible medicament.

In some embodiments, the ingesting of the vibrating gastrointestinal capsule is simultaneous with the ingesting of the ingestible medicament.

In some embodiments, the method further includes timing the vibration mode of operation to at least partially transpire within 5 hours, within 4 hours, within 3.5 hours, within 3 hours, within 2.5 hours, within 2 hours, within 1.5 hours, within 1 hour, or within 0.5 hours of the ingesting of the ingestible medicament.

In some embodiments, the ingestible medicament is at least partially absorbable in a stomach of a subject or in the stomach of the subject. In some embodiments, the ingestible medicament is at least partially absorbable in a small intestine of a subject or in the small intestine of the subject.

In some embodiments, the ingestible medicament for treatment of Parkinsonism includes levodopa. In some embodiments, the ingestible medicament for treatment of Parkinsonism includes at least one dopaminergic agent. In some embodiments, the ingestible medicament for treatment of Parkinsonism includes at least one catecholamine precursor. In some embodiments, the at least one catecholamine precursor includes a dopamine precursor. In some such embodiments, the dopamine precursor includes at least one dopamine precursor agent such as (L)-3,4-dihydroxyphenyl-alanine. In some embodiments, the ingestible medicament for treatment of Parkinsonism includes N-methyl-N-(2-propynyl)-2-methyl-1-phenylethyl-2-amine. In some embodiments, the ingestible medicament for treatment of Parkinsonism includes tyrosine hydroxylase. In some embodiments, the ingestible medicament for treatment of Parkinsonism includes apomorphine. In some embodiments, the ingestible medicament for treatment of Parkinsonism includes at least one anticholinergic agent. In some embodiments, the ingestible medicament for treatment of Parkinsonism includes at least one agent selected to antagonize at least one cholinergic receptor. In some embodiments, the ingestible medicament for treatment of Parkinsonism includes at least one of benzhexol and orphenadrine. In some embodiments, the ingestible medicament for treatment of Parkinsonism includes at least one selective allosteric potentiator of metabotropic glutamate receptor 4 (mGluR4), optionally N-phenyl-7-(hydroxylimino)cyclopropa[b]chromen-1a-carboxamide.

In some embodiments, the medicament for treatment of Parkinsonism is adapted to delay an onset of Parkinsonism. In some embodiments, the medicament for treatment of Parkinsonism is adapted to mitigate or retard a development of Parkinsonism. In some embodiments, the medicament for treatment of Parkinsonism is adapted to manage a condition of Parkinsonism.

In some embodiments, the vibration mode of operation at least partially transpiring within at least one of an estimated absorption time period and an actual absorption time period of the ingestible medicament within the gastrointestinal tract of the subject the effects an increased absorption of the ingestible medicament for treatment of Parkinsonism, thereby improving a therapeutic efficacy of the medicament.

In some embodiments, the vibration mode of operation at least partially transpiring within at least one of an estimated absorption time period and an actual absorption time period of the ingestible medicament within the gastrointestinal tract of the subject effects an increased absorption of the ingestible medicament for treatment of Parkinsonism, thereby enabling the use of a lower dosage of the medicament, optionally without impairing or diminishing therapeutic efficacy.

In some embodiments, the vibration mode of operation is effected within the gastrointestinal tract so as to stimulate the enteric nervous system of the subject. In some embodiments, the vibration mode of operation is effected within the gastrointestinal tract so as to induce at least one peristaltic wave in a wall of the gastrointestinal tract. In some embodiments, the vibration mode of operation is effected within the gastrointestinal tract so as to effect increasing peristalsis in a wall of the gastrointestinal tract. In some embodiments, increasing peristalsis is effected so as to stimulate the enteric nervous system of the subject.

In some embodiments, the vibrating gastrointestinal capsule is adapted and/or dimensioned to transit the gastrointestinal tract of the subject or of a subject.

In some embodiments, the capsule further includes a control mechanism adapted, in response to receipt of an activation input, to activate the vibrating agitation mechanism to operate in the vibration mode of operation.

In some embodiments, the capsule further includes at least one sensor adapted to provide the activation input.

In some embodiments, the at least one sensor includes an illumination sensor, and the receiving the at least one activation input includes receiving input indicating transition of the capsule from an illuminated environment to a dark environment.

In some embodiments, the at least one sensor includes a pressure sensor and the receiving the at least one activation input includes receiving input indicting pressure applied to the capsule, which pressure is indicative of the capsule moving through a pharynx of the subject.

In some embodiments, the at least one sensor includes a temperature sensor, and the receiving the at least one activation input includes receiving input indicating transition of the capsule from an area with ambient temperature to an area with a human body temperature.

In some embodiments, the at least one sensor includes an accelerometer, and the receiving the at least one activation input includes receiving the activation input in response to a detected activation motion carried out with the gastrointestinal capsule.

In some embodiments, the at least one sensor includes a moisture sensor, and the receiving the at least one activation input includes receiving input indicating transition of the capsule from a dry environment to a humid environment.

In some embodiments, the receipt of the activation input includes receiving the activation input from a control unit remote from the gastrointestinal capsule. In some embodiments, receiving the activation input includes receiving the activation input following the ingesting. In some embodiments, receiving the activation input includes receiving the activation input prior to the ingesting. In some embodiments, receiving the activation input additionally includes receiving a vibration protocol to be used by the control mechanism to control operation of the vibrating agitation mechanism.

In some embodiments, the vibrating agitation mechanism includes at least a radial agitation mechanism, and the controlling includes controlling the radial agitation mechanism, in the vibration mode of operation, to exert radial forces on the housing, in a radial direction with respect to a or the longitudinal axis of the housing, thereby to cause the vibrations exerted by the housing.

In some embodiments, the vibrating agitation mechanism includes at least an axial agitation mechanism, and wherein the control mechanism is adapted to control the axial agitation mechanism, in the vibration mode of operation, to exert axial forces on the housing, in an axial direction with respect to a or the longitudinal axis of the housing, thereby to cause the vibrations exerted by the housing.

In some embodiments, the control mechanism is adapted to control the vibrating agitation mechanism, in the vibration mode of operation, to exert radial forces on the housing in a radial direction with respect to a or the longitudinal axis of the housing and to exert axial forces on the housing in an axial direction with respect to a or the longitudinal axis of the housing, thereby to cause the vibrations exerted by the housing.

In some embodiments, the vibrating agitation mechanism includes a radial agitation mechanism adapted to exert the radial forces and a separate axial agitation mechanism adapted to exert the axial forces.

In some embodiments, the vibrating agitation mechanism includes a single agitation mechanism adapted to exert the radial forces and the axial forces.

In some embodiments, the control mechanism is adapted to control the vibrating agitation mechanism such that the vibrating mode of operation includes a plurality of cycles, each of the cycles including a vibration duration followed by a repose duration, wherein the housing exerts the vibrations during the vibration duration.

In some embodiments, the repose duration is greater than the vibration duration.

In some embodiments, the vibration duration is in the range of 0.1 second to 10 seconds, 1 second to 10 seconds, 1 second to 9 seconds, 2 seconds to 9 seconds, 3 seconds to 9 seconds, 3 seconds to 8 seconds, 3 seconds to 7 seconds, 3 seconds to 6 seconds, 4 seconds to 6 seconds, or 5 seconds to 6 seconds.

In some embodiments, the repose duration is in the range of 1 second to 180 seconds, 3 seconds to 180 seconds, 5 seconds to 180 seconds, 5 seconds to 150 seconds, 5 seconds to 120 seconds, 8 seconds to 100 seconds, 8 seconds to 30 seconds, 10 seconds to 80 seconds, 10 seconds to 70 seconds, 10 seconds to 60 seconds, 10 seconds to 50 seconds, 10 seconds to 40 seconds, 10 seconds to 30 seconds, 10 seconds to 20 seconds, or 15 seconds to 20 seconds.

In some embodiments, a duration of each of the plurality of cycles is in the range of 1.1 seconds to 200 seconds, 5 seconds to 200 seconds, 10 seconds to 200 seconds, 10 seconds to 150 seconds, 10 seconds to 100 seconds, 10 seconds to 80 seconds, 10 seconds to 50 seconds, 10 seconds to 40 seconds, 10 seconds to 30 seconds, 15 seconds to 50 seconds, 15 seconds to 40 seconds, 15 seconds to 30 seconds, or 15 seconds to 25 seconds.

In some embodiments, the control mechanism is adapted to control the vibrating agitation mechanism such that a cumulative duration of the vibrating mode of operation is in the range of 1 hour to 12 hours, 2 hours to 10 hours, 2 hours to 8 hours, 2 hours to 6 hours, 2 hours to 4 hours, or 2 hours to 3 hours.

In some embodiments, in the first vibration mode of operation, the vibrating agitation mechanism is configured such that a net force exerted by the housing on the environment is in the range of 50 grams-force to 600 grams-force.

In some embodiments, in the first vibration mode of operation the vibrating agitation mechanism is configured to exert the forces on the housing to attain a vibrational frequency within a range of 10 Hz to 650 Hz, 15 Hz to 600 Hz, 20 Hz to 550 Hz, 30 Hz to 550 Hz, 50 Hz to 500 Hz, 70 Hz to 500 Hz, 100 Hz to 500 Hz, 130 Hz to 500 Hz, or 150 Hz to 500 Hz.

In accordance with a further embodiment of the present invention, there is provided a method of using a vibrating gastrointestinal capsule in coordination with an ingestible medicament for treatment of Parkinsonism, the method including:
(a) providing the vibrating gastrointestinal capsule, the capsule including:
   a housing;
   a vibrating agitation mechanism adapted such that, in a vibration mode of operation, the housing exerts vibrations on an environment surrounding the vibrating gastrointestinal capsule;
   a power supply disposed within the housing and adapted to power the vibrating agitation mechanism; and
   a control mechanism adapted to activate the vibrating agitation mechanism to operate in the vibration mode of operation;
(b) ingesting the vibrating gastrointestinal capsule;
(c) ingesting the ingestible medicament; and
(d) controlling at least one of a time of ingesting the vibrating gastrointestinal capsule and a timing of the vibration mode of operation such that the vibration mode at least partially transpires within a particular time period with respect to the ingesting of the ingestible medicament.

In some embodiments, the particular time period is within 5 hours, within 4 hours, within 3.5 hours, within 3 hours, within 2.5 hours, within 2 hours, within 1.5 hours, within 1 hour, or within 0.5 hours of the ingesting of the ingestible medicament.

In some embodiments, controlling includes both controlling the time of ingesting the vibrating gastrointestinal capsule and the timing of the vibration mode of operation.

In some embodiments, controlling is effected so as to improve absorption of the ingestible medicament within a gastrointestinal tract of a subject.

In accordance with another embodiment of the present invention, there is provided a method of using a vibrating gastrointestinal capsule in coordination with an ingestible medicament for treatment of Parkinsonism, the method including:
(a) providing the vibrating gastrointestinal capsule, the capsule including:
   a housing;
   a vibrating agitation mechanism adapted such that, in a vibration mode of operation, the housing exerts vibrations on an environment surrounding the vibrating gastrointestinal capsule;
   a power supply disposed within the housing and adapted to power the vibrating agitation mechanism; and
   a control mechanism adapted to activate the vibrating agitation mechanism to operate in the vibration mode of operation;
(b) ingesting the ingestible medicament;
(c) ingesting the vibrating gastrointestinal capsule; and
(d) controlling at least one of a time of the ingesting of the vibrating gastrointestinal capsule and a timing or activation delay of the vibration mode of operation, such that the vibration mode of operation at least partially transpires within an estimated absorption time period of the ingestible medicament within the gastrointestinal tract of the subject.

In accordance with a further embodiment of the present invention, there is provided a method of using a vibrating gastrointestinal capsule in coordination with an ingestible medicament for treatment of Parkinsonism, the method including:
(a) providing the vibrating gastrointestinal capsule, the capsule including:
   a housing;
   a vibrating agitation mechanism adapted such that, in a vibration mode of operation, the housing exerts vibrations on an environment surrounding the vibrating gastrointestinal capsule;
   a power supply disposed within the housing and adapted to power the vibrating agitation mechanism; and
   a control mechanism adapted to activate the vibrating agitation mechanism to operate in the vibration mode of operation;
(b) ingesting the ingestible medicament;
(c) ingesting the vibrating gastrointestinal capsule; and
(d) controlling at least one of a time of the ingesting of the vibrating gastrointestinal capsule and a timing or activation delay of the vibration mode of operation, such that the vibration mode of operation at least partially transpires within an actual absorption time period of the ingestible medicament within the gastrointestinal tract of the subject.

In accordance with yet another embodiment of the present invention, there is provided a kit for promoting absorption of an ingested medicament into the blood stream, the kit including:
   a medicament to be ingested; and
   vibrating ingestible capsule including:
   a vibrating agitation mechanism adapted such that, in a vibration mode of operation, the housing exerts vibrations on an environment surrounding the vibrating gastrointestinal capsule;
   a power supply disposed within the housing and adapted to power the vibrating agitation mechanism; and
   a control mechanism adapted to activate the vibrating agitation mechanism to operative in the vibration mode of operation, the control mechanism adapted to control a timing or activation delay of the vibration mode of operation such that the vibration mode of operation at least partially transpires within at least one of an estimated absorption time period and an actual absorption time period of the ingested medicament within the gastrointestinal tract of the subject.

In accordance with a further embodiment of the present invention, there is provided use of a vibrating ingestible capsule for promoting absorption of an ingested medicament into the blood stream, the vibrating ingestible capsule including:
   a housing;
   a vibrating agitation mechanism adapted such that, in a vibration mode of operation, the housing exerts vibrations on an environment surrounding the vibrating gastrointestinal capsule;
   a power supply disposed within the housing and adapted to power the vibrating agitation mechanism; and
   a control mechanism adapted to activate the vibrating agitation mechanism to operative in the vibration mode of operation, the control mechanism adapted to control a timing or activation delay of the vibration mode of operation such that the vibration mode of operation at least partially transpires within at least one of an estimated absorption time period and an actual absorption time period of the ingested medicament within the gastrointestinal tract of the subject.

BRIEF DESCRIPTION OF THE FIGURES

The foregoing discussion will be understood more readily from the following detailed description of the invention, when taken in conjunction with the accompanying FIGS. 1-2), in which.

DESCRIPTION OF THE PREFERRED EMBODIMENTS

Figure 1:
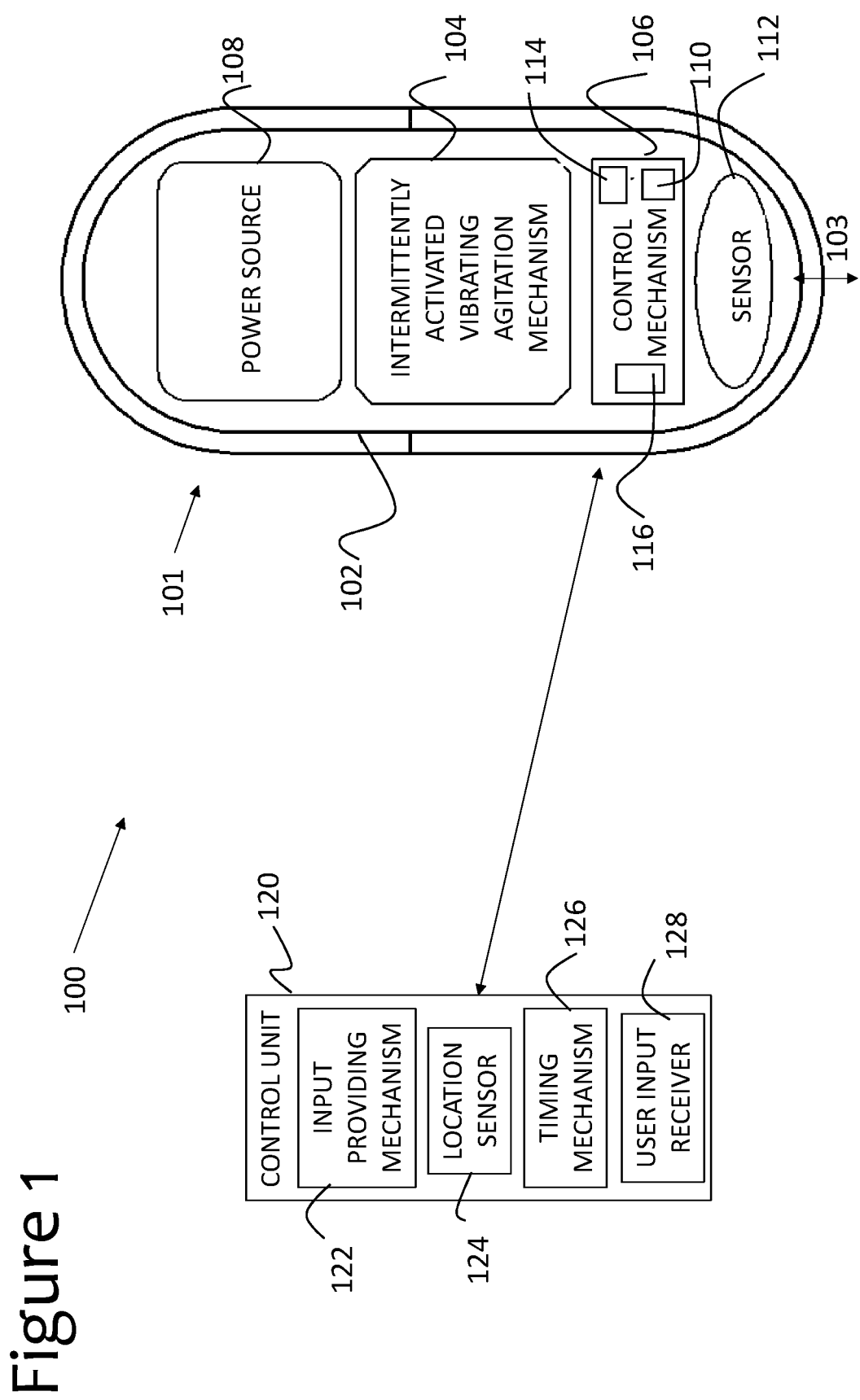
FIG. 1 is a schematic block diagram of a gastrointestinal treatment system including a vibrating ingestible capsule according to an embodiment of the present invention.

The principles of the inventive gastrointestinal treatment system and method of enhancing the absorption into the bloodstream of ingestible medicaments for treating Parkinsonism using the inventive gastrointestinal treatment system, may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

For the purposes of this application, the term "subject" relates to a human.

For the purposes of this application, the term "vibrating ingestible capsule" relates to an ingestible capsule adapted to at least intermittently vibrate, for a cumulative duration of at least one minute, in accordance with a vibration protocol of the capsule.

For the purposes of this application, the term "vibrating agitation mechanism" refers to any type of mechanism that vibrates or causes elements in its vicinity to vibrate, including a vibration motor or engine and a pendulum.

For the purposes of this application, the term "intermittently activated vibrating agitation mechanism" refers to a vibration agitation mechanism that vibrates or causes elements in its vicinity to vibrate and is operative at certain times, and does not vibrate or cause elements in its vicinity to vibrate at other times, the activation times being selected by a control mechanism or other control unit controlling the vibration agitation mechanism.

For the purposes of this application, the term "vibration protocol" relates to a protocol specifying vibration parameters of an intermittently activated vibrating agitation mechanism of a vibrating ingestible capsule. Typically, the vibration protocol relates to an activation delay for initiating vibration (e.g., a duration between "initial" activation of the capsule and the first activation of the vibration agitation mechanism), a vibration rate (number of vibration cycles per hour), a vibration duration and a repose duration for each vibration cycle, a vibration frequency, an amount of force exerted by the vibrations, and the like.

For the purposes of this application, the term "treatment procedure" relates to parameters of a treatment utilizing vibrating ingestible capsules, which are typically defined by a treating physician or medical practitioner. For example, the treatment procedure may include the number of capsules to be taken within a specific time duration (e.g., 3 capsules per week, 2 capsules per day), the frequency at which capsules should be taken, the time of day at which capsules should be taken, whether the capsule should be taken with or without food, and the like.

For the purpose of this application, the term "treatment protocol" relates to all aspects of treatment of a subject with a vibrating ingestible capsule, and includes the treatment procedure as well as the vibration protocol to be used for treating the subject.

For the purpose of this application, the term "activation input" relates to an input received by a control mechanism or control mechanism of a vibrating ingestible capsule, which causes the control mechanism or control mechanism of the capsule to activate itself, so as to be able to process inputs and/or to control additional components of the capsule. The activation input may be received from an element forming part of the capsule, such as a sensor sensing specific conditions in which the capsule should be activated, or from a remote source, such as a remote control mechanism, for example by way of a signal transmitted to the capsule, magnetic field applied to the capsule, specific motion applied to the capsule, or any other type of input provided to the capsule from a remote source.

For the purpose of this application, a vibrating ingestible capsule is said to be in an "inoperative state" when the capsule is in a storage condition, intended to preserve the life of a battery thereof. In the inoperative state, components of the capsule which are intended to receive or to provide an activation input, such as specific sensors, transceivers, and/or timing mechanisms may be active at least to a minimal degree. However, in the inoperative state, no vibration takes place, and a control mechanism controlling vibration of the capsule is inactive.

For the purpose of this application, a vibrating ingestible capsule is said to be in an "operative state" when the control mechanism of the capsule is processing inputs and data, and can cause a vibrating agitation mechanism of the capsule to vibrate or cause elements in its vicinity to vibrate.

For the purpose of this application, an "ingestible medicament" is at least partially absorbable to the bloodstream from within the stomach, small intestine, and large intestine, and more typically, within the stomach or small intestine.

For the purpose of this application, the term "partially absorbable" is meant to include the possibility that the environment within the gastrointestinal tract (including acids, enzymes, etc. thereof) may chemically modify the ingested medicament in order to achieve the characteristic "partially absorbable".

For the purpose of this application, an estimated absorption time may be determined as follows:

(i) ingestible medicaments that are absorbed in the stomach have an estimated absorption time within a range of 0.5 to 1.5 hours from the time of ingestion of the medicament;

(ii) ingestible medicaments that are absorbed in the small intestine have an estimated absorption time within a range of 1.0 to 5 hours from the time of ingestion of the medicament;

(iii) ingestible medicaments that are absorbed in both the stomach and the small intestine have an estimated absorption time within a range of 0.5 to 5 hours from the time of ingestion of the medicament;

(iv) ingestible medicaments that are absorbed in the large intestine have an estimated absorption time of at least 4 hours, and more typically, within a range of 4 to 30 hours, 6 to 30 hours, 6 to 20 hours, or 8 to 20 hours from the time of ingestion of the medicament.

The location within the GI tract at which the particular ingestible medicament is absorbed to the bloodstream may often be public knowledge. This location may be provided by, or known to, the manufacturer and/or distributor of the particular ingestible medicament. Alternatively or additionally, the location may be known to relevant medical practitioners, including doctors and pharmacists, and more particularly, to a medical practitioner of the subject.

For the purpose of this application, an actual absorption time may be determined from clinical data, in vivo or in vitro, according to accepted clinical procedures known to those of skill in the art. Since actual absorption is achieved over a period of time, the "actual absorption time" or "actual absorption time period" may be defined by the time period at which between 20% and 80% of the absorption occurs. In the absence of such data, the "actual absorption time" or "actual absorption time period" may be defined by determining the "peak" actual absorption time, and building a time period of up to 1 hour on each side of the peak time.

For the purpose of this application, the term "Parkinsonism" is meant to include Parkinson's disease, or symptoms of neurodegeneration associated therewith.

For the purpose of this application, the term "Parkinsonism" is meant to include progressive supranuclear palsy, or symptoms of neurodegeneration associated therewith.

For the purpose of this application, the term "Parkinsonism" is meant to include corticobasal degeneration, or symptoms of neurodegeneration associated therewith.

For the purpose of this application, the term "Parkinsonism" is meant to include multiple system atrophy, or symptoms of neurodegeneration associated therewith.

For the purpose of this application, the term "Parkinsonism" is meant to include Parkinson-plus syndromes (also known as disorders of multiple system degeneration), or symptoms of neurodegeneration associated therewith.

For the purpose of this application, the term "Parkinsonism" is meant to include any neurodegenerative disease in which the subject exhibits at least one (and typically at least two or three) of the classical features of Parkinson's disease: tremor, postural instability, and akinesia or bradykesia.

For the purpose of this application, the term "Parkinsonism" is meant to include any neurodegenerative disease in which the subject positively responds to a dopaminergic treatment.

For the purpose of this application, the term "Parkinsonism" is meant to include any neurodegenerative disease in which the particular subject positively responds to an anticholinergic treatment.

For the purpose of this application, the term "Parkinsonism" is meant to include any neurodegenerative disease in which a dopaminergic treatment is clinically utilized to treat the sufferers or subjects.

For the purpose of this application, the term "Parkinsonism" is meant to include any neurodegenerative disease in which an anticholinergic treatment is clinically utilized to treat the sufferers or subjects.

For the purpose of this application, the term "Parkinson's disease" (PD) is meant as used by those of skill in the art of neurodegenerative diseases. It is believed that PD is due to the loss of brain cells that produce dopamine. Early signs and symptoms of Parkinson's disease include at least one of tremors (or trembling), slowness of movement, body rigidity and stiffness, and gait problems.

For the purpose of this application, the term "treatment of Parkinsonism" and the like refers to at least one of: (i) delaying onset of Parkinsonism (e.g., PD); (ii) mitigating the development of Parkinsonism (e.g., PD); and (iii) managing a condition of Parkinsonism (e.g., PD).

For the purpose of this application, the term "managing a condition of", with respect to Parkinsonism and the like, is meant to include, inter alia, improving absorption of a medicament, such as a medicament used in the treatment of Parkinsonism (e.g., levodopa), into the bloodstream. Such condition management may be manifested by at least one of (i) improved medicament efficacy due to the increased absorption; and (ii) reduced dosage of the medicament, due to the increased medicament absorption efficacy.

Referring now to the drawings, FIG. 1 is a schematic block diagram of a gastrointestinal treatment system 100 including a vibrating ingestible capsule 101 according to an embodiment of the present invention.

As seen in FIG. 1, gastrointestinal treatment system 100 includes vibrating ingestible capsule 101. Capsule 101 includes a capsule housing or shell 102, arranged along a longitudinal axis 103 and having disposed therein a vibrating agitation mechanism 104. A control mechanism 106, which may for example be, or include, a processor, is adapted to control operation of vibrating agitation mechanism 104, and at least one power source 108 provides power to vibrating agitation mechanism 104 and control mechanism 106.

Power source 108 may be any suitable power source, such as one or more alkaline or silver oxide batteries, primary batteries, rechargeable batteries, capacitors and/or supercapacitors.

Intermittently activated vibrating agitation mechanism 104 is adapted to have a vibration mode of operation (also termed the first mode of operation) and a rest mode of operation (also termed the second mode of operation). In the vibration mode of operation, intermittently activated vibrating agitation mechanism 104 is adapted to exert forces on capsule housing 102, such that capsule housing 102 exerts vibrations on an environment surrounding capsule 101.

In some embodiments, the capsule is in an inoperative state, until the receipt of an activation input, which causes control mechanism 106 to transition the capsule from the inoperative state to an operative state.

In some embodiments, control mechanism 106 is functionally associated with, or includes, a timing mechanism 110, powered by power source 108 and adapted to track at least one time characteristic, such as a duration that has passed since an activation input was received, or a duration that has passed since the subject ingested capsule 101.

In some embodiments, capsule 101 is devoid of any sensors for sensing an environment thereof. In some such embodiments, control mechanism 106 is adapted, in response to receipt of an activation input, to wait a predetermined delay time, and following the predetermined delay time, to activate vibrating agitation mechanism 104 to operate in said first vibration mode of operation.

In other embodiments, such as the embodiment illustrated in FIG. 1, capsule 101 further includes at least one sensor 112, functionally associated with control mechanism 106. The at least one sensor 112 may be adapted to sense at least one parameter within capsule 101 or in an environment of capsule 101, and may include a temperature sensor, an illumination sensor, a moisture sensor, a pressure sensor, an accelerometer, or any other suitable sensor. In some embodiments, the at least one sensor 112 is adapted to identify a specific condition in capsule 101 or in the vicinity thereof, and to provide an activation input to control mechanism 106 in response to identification of the condition. For example, in some embodiments the condition is indicative of the subject ingesting capsule 101.

For example, in some embodiments sensor 112 may include an illumination sensor, adapted to identify transition of capsule 101 from an illuminated environment (e.g. outside the human body) to a dark environment (e.g. within the human body) and to provide an activation input in response to identification of such a transition.

As another example, in some embodiments sensor 112 may include a motion or acceleration sensor, such as an accelerometer, adapted to identify an activation motion carried out by a user on capsule 101 and to provide an activation input in response to identification of such a transition. An example of an accelerometer providing an activation input for a gastrointestinal capsule is provided in U.S. patent application Ser. No. 15/168,065, filed on May 29, 2016, which is incorporated by reference for all purposes as if fully set forth herein.

As another example, in some embodiments sensor 112 may include a pressure sensor adapted identify pressure applied to the capsule 101, which pressure is indicative of the capsule moving through a pharynx of the subject, and to provide an activation input in response to identification of such pressure.

As a further example, in some embodiments sensor 112 may include a temperature sensor adapted to identify transition of capsule 101 from an area with ambient temperature (e.g. outside the human body) to an area with a human body temperature and to provide an activation input in response to identification of such a transition.

As another example, in some embodiments sensor 112 may include a motion or acceleration sensor, such as an accelerometer, adapted to identify an activation motion carried out by a user on capsule 101 and to provide an activation input in response to identification of such a transition.

As a further example, in some embodiments sensor 112 may include a moisture sensor adapted to identify transition of capsule 101 from a dry area (e.g. outside the human body) to a moist area (e.g. within the human body) and to provide an activation input in response to identification of such a transition.

In some embodiments, system 100 further includes a control unit 120, which may be remote from capsule 101, and which is adapted to provide one or more inputs to the capsule. In some such embodiments, capsule 101 further includes a remote input receiving mechanism 116, functionally associated with control mechanism 106, and adapted to receive inputs from an input providing mechanism 122 of control unit 120.

In some embodiments, control unit 120 may further include a timing mechanism 126, adapted to track at least one time characteristic, such as a duration that has passed since a control instruction was provided to capsule 101.

In some embodiments, control unit 120 may further include a user input receiver 128, such as a keyboard, touch screen, or touch pad, adapted to receive input from a user, such as the subject, a medical professional treating the subject, or a caregiver of the subject.

Control unit 120 may be any suitable type of control unit. In some embodiments, control unit may be a suitably configured smart phone or a tablet computer.

In some such embodiments, control unit 120 may provide inputs to capsule 101 by remotely transmitting the inputs from input providing mechanism 122 to remote input receiving mechanism 116, for example using a short range wireless communication method, such as radio frequency (RF) communication or Bluetooth® communication. One example of such a mechanism for providing input to a capsule is described in U.S. patent application Ser. No. 15/132,039 filed Apr. 18, 2016 and entitled "IN VIVO DEVICE AND METHOD OF USING THE SAME", which is incorporated by reference for all purposes as if fully set forth herein.

In some embodiments, control unit 120 is adapted to provide the activation input to control mechanism 106 of capsule 101. In some such embodiments, control unit 120 provides the activation input prior to the subject ingesting capsule 101, whereas in other embodiments control unit 120 provides the activation input following ingestion of capsule 101 by the subject.

Relating to the characteristics of vibrating agitation mechanism 104, the vibrating agitation mechanism may be any suitable mechanism that can be intermittently activated and can apply suitable forces onto capsule housing 102.

In some embodiments, intermittently activated vibrating agitation mechanism 104 may include a radial agitation mechanism adapted to exert radial forces on capsule housing 102, in a radial direction with respect to the longitudinal axis of housing 102. For example, the radial agitation mechanism may include an unbalanced weight attached to a shaft of an electric motor powered by said battery, substantially as described in U.S. Pat. No. 9,707,150, which is incorporated by reference for all purposes as if fully set forth herein.

In some embodiments, intermittently activated vibrating agitation mechanism 104 may include an axial agitation mechanism adapted to exert radial forces on the capsule housing 102, in an axial direction with respect to a longitudinal axis of housing 102. For example, the axial agitation mechanism may include an electric motor powered by the battery and an urging mechanism, associated with, and driven by, the electric motor, such that the urging mechanism adapted to exert said axial forces, substantially as described in U.S. Pat. No. 9,707,150. In some embodiments, the urging mechanism adapted to exert the axial forces in opposite directions. In some embodiments, the urging mechanism is adapted to deliver at least a portion of the axial forces in a knocking mode.

In some embodiments, the forces exerted by intermittently activated vibrating agitation mechanism 104 on capsule housing 102 in the vibration mode of operation include radial forces in a radial direction with respect to the longitudinal axis of the housing and axial forces in an axial direction with respect to the longitudinal axis. In some embodiments, a single agitation mechanism exerts both the radial and the axial forces. In other embodiments, the axial forces are exerted by one agitation mechanism, and the radial forces are exerted by another, separate, agitation mechanism, where both agitation mechanisms form part of intermittently activated vibrating agitation mechanism 104.

In some embodiments, the intermittently activated vibrating agitation mechanism 104 may include a magnet mounted onto a rotor adapted to exert a magnetic field as well as radial forces on capsule housing 102. For example, such a magnetic vibration agitation mechanism is described in U.S. patent application Ser. No. 15/058,216 filed on Mar. 2, 2016 and entitled "PHYSIOTHERAPY DEVICE AND METHOD FOR CONTROLLING THE PHYSIOTHERAPY DEVICE", which is incorporated by reference for all purposes as if fully set forth herein.

In some embodiments, housing 102 may include first and second members, and vibrating agitation mechanism 104 may include a mechanism adapted to effect a vibration by moving the first member of the housing in the opposite direction relative to the second member of the housing, substantially as described in U.S. Pat. No. 9,078,799, which is incorporated by reference for all purposes as if fully set forth herein.

In some embodiments, housing 102 may include a vibration agitation mechanism 104 which makes use of a pendulum to cause vibration in the vicinity of the capsule, for example as described in CN Patent Application Number 105997466 filed on Jun. 16, 2016 and entitled "INTELLIGENT VIBRATING ELECTRONIC CAPSULE", which is incorporated by reference for all purposes as if fully set forth herein.

In the vibrating mode of operation, intermittently activated vibrating agitation mechanism 104 is adapted to have a plurality of vibration cycles, where each cycle includes a vibration duration followed by a repose duration. Forces are exerted by the vibrating agitation mechanism 104 on capsule housing 102 only during the vibration duration, and as such capsule housing 102 only exerts forces on an environment thereof during the vibration duration.

In some embodiments, the number of vibration cycles per hour is in the range of 20 to 400, 40 to 400, 60 to 400, 80 to 400, 40 to 380, 60 to 380, 80 to 380, 40 to 360, 60 to 360, 80 to 360, 100 to 360, 100 to 330, 100 to 300, 100 to 280, 100 to 250, 100 to 220, 100 to 200, 120 to 300, 120 to 280, 120 to 250, 120 to 220, 120 to 200, 150 to 300, 150 to 280, 150 to 250, 150 to 220, 150 to 200, 170 to 300, 170 to 250, 170 to 220, or 170 to 200.

In some embodiments, the repose duration is greater than the vibration duration. In some embodiments, the vibration duration is in the range of 0.1 second to 10 seconds, 1 second to 10 seconds, 1 second to 9 seconds, 2 seconds to 9 seconds, 3 seconds to 9 seconds, 3 seconds to 8 seconds, 3 seconds to 7 seconds, 3 seconds to 6 seconds, or 4 seconds to 6 seconds.

In some embodiments, the repose duration is in the range of 1 second to 180 seconds, 3 seconds to 180 seconds, 5 seconds to 180 seconds, 5 seconds to 150 seconds, 5 seconds to 120 seconds, 8 seconds to 100 seconds, 8 seconds to 30 seconds, 10 seconds to 80 seconds, 10 seconds to 70 seconds, 10 seconds to 60 seconds, 10 seconds to 50 seconds, 10 seconds to 40 seconds, 10 seconds to 30 seconds, 10 seconds to 20 seconds, or 15 seconds to 20 seconds.

In some embodiments, the total duration of one vibration cycle is in the range of 1.1 seconds to 200 seconds, 5 seconds to 200 seconds, 10 seconds to 200 seconds, 10 seconds to 150 seconds, 10 seconds to 100 seconds, 10 seconds to 80 seconds, 10 seconds to 50 seconds, 10 seconds to 40 seconds, 10 seconds to 30 seconds, 15 seconds to 50 seconds, 15 seconds to 40 seconds, 15 seconds to 30 seconds, or 15 seconds to 25 seconds.

In some embodiments, the cumulative duration of the vibrating mode of operation, or the cumulative duration during which vibration cycles are occurring, is in the range of 1 hour to 12 hours, 2 hours to 10 hours, 2 hours to 8 hours, 2 hours to 6 hours, 2 hours to 4 hours, or 2 hours to 3 hours. It will be appreciated that the cumulative duration of vibration cycles may be dependent on properties of power source 108.

It will be appreciated by persons skilled in the art that the vibration mode of operation may be intermittent, or interrupted, such that vibrating agitation mechanism 104 is operative in the vibration mode for a first duration, for example 30 minutes, then does not have any vibration cycles for a second duration, for example 1 hour, and then is operative in the vibration mode and has vibration cycles for a third duration, for example two hours. The cumulative duration relates to the sum of all durations during which vibrating agitation mechanism 104 was operative in the vibration mode and included vibration cycles, including the vibration duration and the repose duration of the vibration cycle.

In some embodiments, vibrating agitation mechanism 104 is configured to exert forces on the capsule housing 102, such that a net force exerted by the capsule housing 102 on the environment thereof is in the range of 50 grams force (gf) to 600 gf, 50 gf to 550 gf, 100 gf to 550 gf, 100 gf to 500 gf, 150 gf to 500 gf, 200 gf to 500 gf, or 200 gf to 450 gf.

In some embodiments, vibrating agitation mechanism 104 is configured to exert said forces on capsule housing 102 to attain a capsule housing 102 vibrational frequency within a range of 10 Hz to 650 Hz, 15 Hz to 600 Hz, 20 Hz to 550 Hz, 30 Hz to 550 Hz, 50 Hz to 500 Hz, 70 Hz to 500 Hz, 100 Hz to 500 Hz, 130 Hz to 500 Hz, or 150 Hz to 500 Hz.

It will be appreciated that the exact specifications of the capsule, such as the specific frequency and force ranges applicable to a specific capsule, are dependent on the specifications of the power source and of the vibrating agitation mechanism.

It will be further appreciated that a specific capsule may be controlled by the control mechanism such that different vibrational frequencies may be attained and/or different net forces may be exerted, by the capsule in different vibration cycles of the capsule. Due to the natural distinction between subjects, use of multiple different parameters in different vibration cycles of a single capsule would allow the capsule to successfully treat multiple subjects, even if the personal optimal treatment for those subjects is not the same, as there is a higher chance that in at least some of the vibration cycles the activation parameters of the capsule would reach, or be close to, the optimal parameters for each specific subject.

Control mechanism 106 is adapted to control the operation of intermittently activated vibrating agitation mechanism 104. Such control may include control of any one or more of the force applied by the vibrating agitation mechanism, the vibrational frequency reached, the times in which vibrating agitation mechanism 104 operates in the vibration mode of operation, the vibration duration of each vibration cycle, the repose duration of each vibration cycle, the vibration cycle duration, and cumulative vibration duration of the vibrating agitation mechanisms.

In some embodiments, control mechanism 106 is adapted to receive information relating to the desired vibration protocol from control unit 120, prior to ingestion of the capsule or to activation thereof, or during the capsule's traversal of the subject's GI tract. For example, the information may be remotely transmitted from control unit 120 to control mechanism 106, for example using a short range wireless communication method. In some embodiments, the information is transmitted as a list of vibration parameters for effecting the vibration protocol. In some embodiments, the information is transmitted as executable code for effecting the first vibration protocol.

In some embodiments, the information includes a desired number of vibration cycles, a desired vibration duration in each vibration cycle, a desired repose duration in each vibration cycle, a desired cumulative vibration duration, and the like.

Control mechanism 106 may be adapted to control vibrating agitation mechanism 104 so that the capsule applies forces to an environment thereof, such that within the gastrointestinal tract, a mechanical stimulation of the wall of the gastrointestinal tract is effected.

Figure 2:
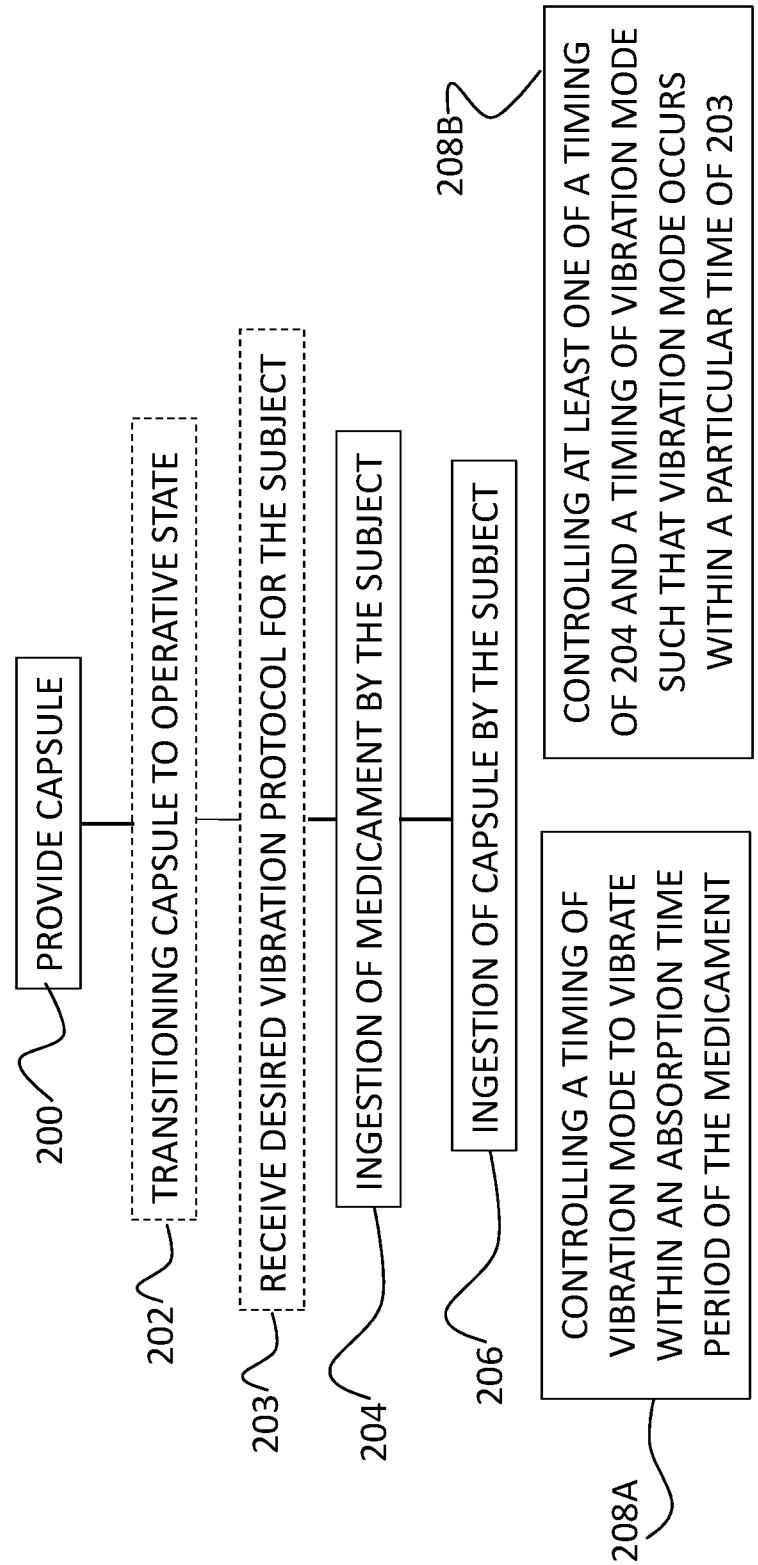
FIG. 2 is a schematic flowchart of a method for using a vibrating gastrointestinal capsule to improve or accelerate the absorption to the blood stream of an ingestible medicament for treatment of Parkinsonism, or to improve the efficacy of such a medicament, according to the present invention, the method being based on use of an ingestible vibrating gastrointestinal capsule, for example as shown in FIG. 1.

Reference is now additionally made to FIG. 2, which is a schematic flowchart of a method for using a vibrating gastrointestinal capsule to improve or accelerate the absorption into the bloodstream of a medicament for treatment of Parkinsonism, and/or to improve the efficacy of such a medicament, according to the present invention. The method may be based on the use of a gastrointestinal capsule system including (or consisting of) a vibrating ingestible capsule, such as capsule 101 of system 100 of FIG. 1.

As seen at step 200, vibrating gastrointestinal capsule is provided. The vibrating gastrointestinal capsule may have, as described with respect to FIG. 1, a housing; a vibrating agitation mechanism adapted such that, in a first vibrating mode ("vibration mode") of operation, the housing exerts vibrations on an environment surrounding the vibrating gastrointestinal capsule; and a power supply disposed within the housing and adapted to power the vibrating agitation mechanism. Typically, the capsule includes an on-board control mechanism adapted to control or activate the vibrating agitation mechanism. The control mechanism may form a component of such a vibrating agitation mechanism.

At step 204, an ingestible medicament for treatment of Parkinsonism is ingested by the subject.

The ingestible medicament for treatment of Parkinsonism may include any one or more of levodopa; at least one dopaminergic agent; at least one catecholamine precursor; a dopamine precursor; at least one dopamine precursor agent, such as (L)-3,4-dihydroxyphenylalanine; N-methyl-N-(2-propynyl)-2-methyl-1-phenylethyl-2-amine; tyrosine hydroxylase; apomorphine; at least one anticholinergic agent; at least one agent selected to antagonize at least one cholinergic receptor; at least one of benzhexol and orphenadrine; at least one selective allosteric potentiator of metabotropic glutamate receptor 4 (mGluR4), such as N-phenyl-7-(hydroxylimino)cyclopropa[b]chromen-1a-carboxamide.

In some embodiments, the ingestible medicament may be ingested directly, for example by ingesting a tablet, capsule, liqui-gel capsule, chewable tablet, syrup, or any other form of dosage including the medicament.

In some embodiments, the ingestible medicament may be ingested within a medicament delivery capsule, adapted to deliver the medicament to a specific location in the gastrointestinal tract. Examples of such medicament delivery capsules are described in:

U.S. Pat. Nos. 5,170,801; 6,632,216; 6,776,165; 6,929,363; 8,202,697; 8,518,022; 8,597,278; and 8,771,730;

U.S. Patent Application Publication Numbers 2004/0253304; 2004/0267240; 2005/0058701; 2005/0148847; 2008/0275430; 2009/0306633; and 2010/0049012; PCT Patent Application Publication Numbers WO2006/025013; WO2008/012700; and WO 2009/063375;

all of which are incorporated by reference for all purposes as if fully set forth herein. At step 206, the vibrating gastrointestinal capsule is ingested by the subject.

While the ingestible medicament and the vibrating gastrointestinal capsule may be ingested at the same time, or within 0-30 minutes of each other, no order of action is implied by FIG. 2, and the capsule may be ingested prior to the medicament.

In some embodiments, the vibrating gastrointestinal capsule functions also as a medicament delivery system for delivery of the ingestible medicament and delivers the medicament to a specific area or location in the gastrointestinal tract of the subject. In such embodiments, the subject ingests a single capsule, the vibrating ingestible capsule, thereby fulfilling steps 204 and 206 of the method.

As shown, step 208A includes controlling at least one of a time of ingesting the vibrating gastrointestinal capsule and a timing of said vibration mode of operation (e.g., when the vibration mode is initiated, a duration of the vibration mode, etc.) to at least partially transpire within at an absorption time period of the ingestible medicament within the gastrointestinal tract of the subject. Typically, the absorption time period is an estimated absorption time period, as defined herein. In some cases, an actual absorption time period may be determined, again, as defined herein.

Additionally or alternatively, the method may include controlling at least one of a timing of ingesting the vibrating gastrointestinal capsule and a timing of said vibration mode of operation such that the vibration mode at least partially transpires within a particular time period with respect to the ingesting of the ingestible medicament (step 208B).

The particular time period may be within 5 hours, within 4 hours, within 3.5 hours, within 3 hours, or within 2.5 hours of the ingesting of the ingestible medicament, and more typically, within 2 hours, within 1.5 hours, within 1 hour, or within 0.5 hours thereof.

In some embodiments, the method may include controlling at least one of a timing of ingesting the vibrating gastrointestinal capsule and a timing of said vibration mode of operation such that said vibration mode at least partially transpires when the capsule is in a region of the gastrointestinal tract in which the medicament is typically absorbed into the bloodstream. The region of the gastrointestinal tract may include one or more of the stomach of the subject, the duodenum of the subject, the small intestine of the subject, the large intestine of the subject, or the colon of the subject.

For example, when cooperating with the medicament levadopa, which is typically absorbed into the bloodstream through the stomach walls and/or the small intestine walls, the vibration mode at least partially transpires within a time period in which the capsule traverses, or is expected to traverse, the stomach and small intestine.

In some embodiments, and as described in further detail herein, the method may include transitioning the capsule (from an inoperative state) to an operative state.

The capsule may be pre-programmed with a vibration protocol. This protocol may include, by way of example, a particular or pre-determined activation time following ingestion, in which the capsule is transitioned from an inoperative state to an operative state.

Alternatively or additionally, the capsule may receive an activation input in an active fashion (e.g., from an external controller via RF) or in a passive fashion (e.g., a signal from a sensor to the on-board controller). It will be appreciated that step 202, in which the vibrating ingestible capsule is transitioned from the inoperative state to the operative state, may be performed after ingestion of the capsule by the subject (e.g., in the case of external control via RF).

In some embodiments, control mechanism 106 may optionally receive a desired vibration protocol for the subject, at an optional step 203.

In some embodiments, providing of the predetermined time(s) at step 202 and/or providing the desired vibration protocol for the subject at step 203 occurs at the time of manufacturing of the capsule, for example by pre-programming the time into the control mechanism.

In some embodiments, providing of the predetermined time(s) at step 202 and/or providing the desired vibration protocol for the subject at step 203 may be effected by a control unit, such as control unit 120 of FIG. 1.

The programming of the vibration protocol may include remotely transmitting the desired vibration protocol from control unit 120 to control mechanism 106, for example using a short-range wireless communication method. In some embodiments, the desired vibration protocol is transmitted as a list of vibration parameters for effecting the vibration protocol. In some embodiments, the desired vibration protocol is transmitted as executable code for effecting the vibration protocol.

As discussed hereinabove, in some embodiments the activation input may be received from the control unit 120 or from sensors within the capsule sensing that the capsule has been ingested or that a user has carried out an activation motion with the capsule.

Substantially as described hereinabove, the vibrating ingestible capsule may be activated prior to the user ingesting the capsule at step 206, for example by a signal from the control unit or by the user carrying out an activation motion. In other embodiments, the activation input is provided at the time of ingestion or immediately thereafter, for example by sensors sensing a change in the environment of the capsule due to its ingestion, as described at length hereinabove. In yet other embodiments, the activation input may be provided remotely when the capsule is already in the body of the subject, for example by remote communication from control module 120.

Following activation of capsule 101, or together therewith, capsule 101 is ingested by the subject, and begins to travel through the gastrointestinal tract of the subject, as evident from step 206.

Operation of vibrating agitation mechanism 104 in the vibrating mode of operation at step 208A or 208B effects vibration of capsule housing 102, as described hereinabove, such that the housing exerts vibrations on the environment surrounding the capsule. Specifically, vibration of capsule housing 102 may be intended to effect a mechanical stimulation of the wall of the gastrointestinal tract at a time when the ingested medicament may be absorbed, thereby to increase or accelerate the absorption of the ingested medicament into the bloodstream of the subject, for delivery to a target treatment region of the medicament.

Typically, the target treatment region of medicaments for treatment of Parkinsonism is in or near the brain, and as such the medicament, absorbed to the bloodstream in the gastrointestinal tract, is delivered to the target treatment region away from the gastrointestinal tract.

A treatment session as defined in FIG. 2 may be repeatedly administered to the subject as specified in the treatment protocol for the subject. In some embodiments, the treatment protocol includes administering a plurality of treatment sessions to the subject. In some embodiments, the treatment protocol includes administering at least one treatment session to the subject per week, over a treatment period of at least two weeks, at least at least three weeks, at least four weeks, at least five weeks, at least six weeks, or at least eight weeks. In some embodiments, the treatment protocol includes administering 1 to 7 treatment sessions per week, 3 to 14 treatment sessions per two weeks, 2 to 7 treatment sessions per week, 5 to 14 treatment sessions per two weeks, 3 to 7 treatment sessions per week, 7 to 14 treatment sessions per two weeks, 4 to 7 treatment sessions per week, or 5 to 7 treatment sessions per week.

This patent application claims the benefit of unpublished U.S. Provisional Patent Application No. 62/655,031 filed on Apr. 9, 2018, the specification, figures, claims and abstract of which are each incorporated herein by reference in their entireties.

It will be appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and previously-published patent applications mentioned in this specification are herein incorporated in their entirety by reference into the specification, to the same extent as if each individual publication, patent or previously-published patent application was specifically and individually indicated to be incorporated herein by reference. In addition, citation or identification of any reference in this application shall not be construed as an admission that such reference is available as prior art to the present invention.

What is claimed is:

1. A method of using a vibrating ingestible capsule in coordination with an ingestible medicament for treatment of Parkinsonism, the method comprising:
   (a) providing the vibrating ingestible capsule, the capsule including:
      a housing;
      a vibrating agitation mechanism adapted such that, in a vibration mode of operation, said housing exerts vibrations on an environment surrounding the vibrating ingestible capsule;
      a power supply disposed within said housing and adapted to power said vibrating agitation mechanism; and
      a control mechanism adapted to activate said vibrating agitation mechanism to operate in said vibration mode of operation;
   (b) ingesting the ingestible medicament;
   (c) ingesting the vibrating ingestible capsule; and
   (d) controlling at least one of a time of said ingesting of the vibrating ingestible capsule and a timing or activation delay of said vibration mode of operation, such that said vibration mode of operation at least partially transpires within at least one of an estimated absorption time period and an actual absorption time period of the ingestible medicament within the gastrointestinal tract of the subject.

2. The method of claim 1, wherein said controlling is effected such that said vibration mode of operation at least partially transpires during said actual absorption time.

3. The method of claim 1, wherein said actual absorption time period occurs when the ingestible medicament is disposed in a small intestine of the subject.

4. The method of claim 1, wherein said controlling of is effected such that said vibration mode of operation at least partially transpires during said estimated absorption time.

5. The method of claim 4, wherein said estimated absorption time is within a range of 0.5 to 5 hours from said ingesting of said ingestible medicament.

6. The method of claim 1, wherein said ingesting of said vibrating ingestible capsule occurs after said ingesting of said ingestible medicament, and transpires within 4 hours of said ingesting of the ingestible medicament.

7. The method of claim 1, wherein said ingesting of said vibrating ingestible capsule is simultaneous with said ingesting of the ingestible medicament.

8. The method of claim 1, further comprising timing said vibration mode of operation to at least partially transpire within 5 hours, within 4 hours, within 3.5 hours, within 3 hours, within 2.5 hours, within 2 hours, within 1.5 hours, within 1 hour, or within 0.5 hours of said ingesting of the ingestible medicament.

9. The method of claim 1, wherein the ingestible medicament for treatment of Parkinsonism includes at least one of:
   levodopa;
   at least one dopaminergic agent;
   at least one catecholamine precursor;
   a dopamine precursor;
   N-methyl-N-(2-propynyl)-2-methyl-1-phenylethyl-2-amine;
   tyrosine hydroxylase;
   apomorphine;
   at least one anticholinergic agent;
   at least one agent selected to antagonize at least one cholinergic receptor;
   at least one of benzhexol and orphenadrine;
   at least one selective allosteric potentiator of metabotropic glutamate receptor 4 (mGluR4);
   N-phenyl-7-(hydroxylimino)cyclopropa[b]chromen-1a-carboxamide.

10. The method of claim 9, wherein the medicament for treatment of Parkinsonism is adapted to delay an onset of Parkinsonism.

11. The method of claim 9, wherein the medicament for treatment of Parkinsonism is adapted to mitigate or retard a development of Parkinsonism.

12. The method of claim 9, wherein the medicament for treatment of Parkinsonism is adapted to manage a condition of Parkinsonism.

13. The method of claim 1, wherein said vibration mode of operation at least partially transpiring within at least one of an estimated absorption time period and an actual absorption time period of the ingestible medicament within the gastrointestinal tract of the subject effects an increased absorption of the ingestible medicament for treatment of Parkinsonism, thereby providing at least one of the following impacts:
   improving a therapeutic efficacy of the medicament; and
   enabling the use of a lower dosage of said medicament than a dosage used without use of said vibrating ingestible capsule, without impairing or diminishing therapeutic efficacy.

14. The method of claim 1, wherein said vibration mode of operation is effected within the gastrointestinal tract so as to achieve at least one of the following results:
   stimulate the enteric nervous system of the subject;
   induce at least one peristaltic wave in a wall of the gastrointestinal tract; and
   effect increasing peristalsis in a wall of the gastrointestinal tract.

15. The method of claim 1, wherein, in said vibration mode of operation, said vibrating agitation mechanism is further adapted to effect at least one of:

(a) exert forces on said housing such that a net force exerted by said housing on said environment is within a range of 50 grams force to 600 grams force;
(b) exert said forces on said housing such that a vibrational frequency of said housing is within a range of 10 Hz to 650 Hz.

16. An arrangement comprising:
(a) a vibrating ingestible capsule for promoting absorption of an ingested medicament into the blood stream, the vibrating ingestible capsule including:
   a housing;
   a vibrating agitation mechanism adapted such that, in a vibration mode of operation, said housing exerts vibrations on an environment surrounding the vibrating ingestible capsule;
   a power supply disposed within said housing and adapted to power said vibrating agitation mechanism; and
   a control mechanism adapted to activate said vibrating agitation mechanism to be operative in said vibration mode of operation, said control mechanism adapted to control a timing or activation delay of said vibration mode of operation such that said vibration mode of operation at least partially transpires within at least one of an estimated absorption time period and an actual absorption time period of the ingested medicament within the gastrointestinal tract of the subject;
   wherein, in said vibration mode of operation, said vibrating agitation mechanism is further adapted to effect at least one of:
   (i) exert forces on said housing such that a net force exerted by said housing on said environment is within a range of 50 grams force to 600 grams force;
   (ii) exert said forces on said housing such that a vibrational frequency of said housing is within a range of 10 Hz to 650 Hz; and
(b) an ingestible medicament for treatment of Parkinsonism.

17. The arrangement of claim 16, wherein the ingestible medicament for treatment of Parkinsonism includes at least one of:
   levodopa;
   at least one dopaminergic agent;
   at least one catecholamine precursor;
   a dopamine precursor;
   N-methyl-N-(2-propynyl)-2-methyl-1-phenylethyl-2-amine;
   tyrosine hydroxylase;
   apomorphine;
   at least one anticholinergic agent;
   at least one agent selected to antagonize at least one cholinergic receptor;
   at least one of benzhexol and orphenadrine;
   at least one selective allosteric potentiator of metabotropic glutamate receptor 4 (mGluR4);
   N-phenyl-7-(hydroxylimino)cyclopropa[b]chromen-1a-carboxamide.

* * * * *